(12) United States Patent
Tanabe

(10) Patent No.: US 7,771,617 B2
(45) Date of Patent: Aug. 10, 2010

(54) CHOLESTERIC LIQUID CRYSTAL COMPOSITION

(75) Inventor: Mayumi Tanabe, Ichihara (JP)

(73) Assignees: Chisso Corporation, Osaka (JP); Chisso Petrochemical Corporation, Tokyo (JP)

( * ) Notice: Subject to any disclaimer, the term of this patent is extended or adjusted under 35 U.S.C. 154(b) by 387 days.

(21) Appl. No.: 12/007,845

(22) Filed: Jan. 16, 2008

(65) Prior Publication Data

US 2008/0175806 A1      Jul. 24, 2008

(30) Foreign Application Priority Data

Jan. 18, 2007    (JP) ............................... 2007-009270

(51) Int. Cl.
*C09K 19/30*    (2006.01)
*C09K 19/20*    (2006.01)
*C09K 19/12*    (2006.01)
*A61Q 1/02*     (2006.01)

(52) U.S. Cl. ........................... 252/299.63; 252/299.64; 252/299.65; 252/299.66; 252/299.67; 424/63

(58) Field of Classification Search ............ 252/299.63, 252/299.64, 299.65, 299.66, 299.67; 424/63, 424/64

See application file for complete search history.

(56) References Cited

U.S. PATENT DOCUMENTS

| 4,784,793 | A | * | 11/1988 | Coates et al. | .......... | 252/299.62 |
| 5,188,815 | A | * | 2/1993 | Coates et al. | ................. | 424/9.8 |
| 5,705,093 | A | | 1/1998 | Coates et al. | .......... | 252/299.01 |
| 7,682,522 | B2 | * | 3/2010 | Tanabe | ................... | 252/299.63 |

FOREIGN PATENT DOCUMENTS

| JP | 56-092836 | 7/1981 |
| JP | 57 040581 | 3/1982 |
| JP | 2004-137158 | 5/2004 |
| WO | WO 86/04328 | 7/1986 |

\* cited by examiner

*Primary Examiner*—Shean C Wu
(74) *Attorney, Agent, or Firm*—Hogan Lovells US LLP

(57) ABSTRACT

The cholesteric liquid crystal composition includes at least one compound selected from the group of compounds represented by Formulas (1) to (8):

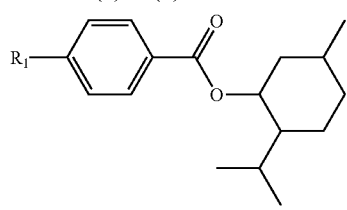

(1)

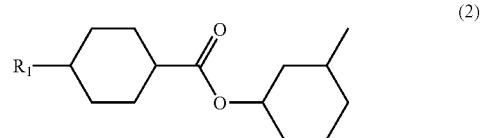

(2)

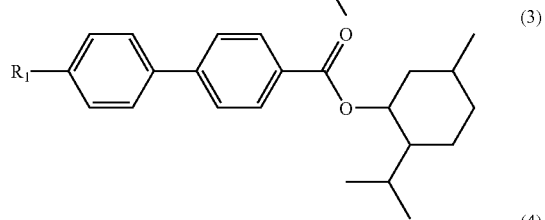

(3)

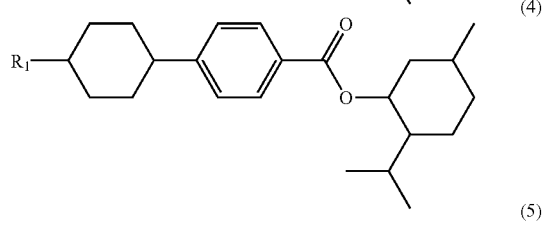

(4)

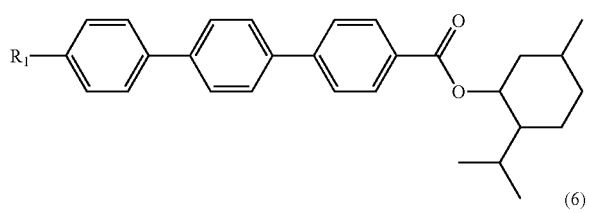

(5)

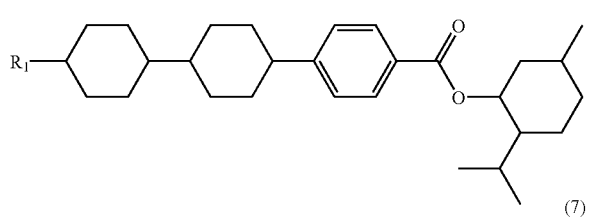

(6)

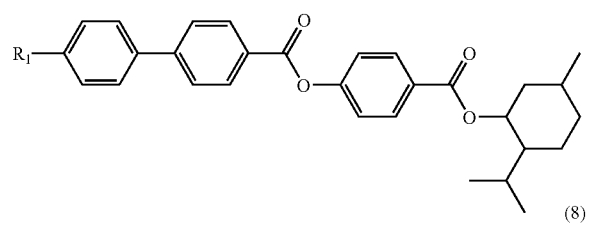

(7)

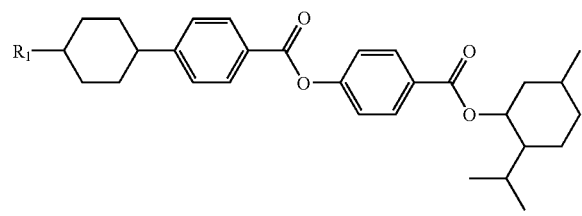

(8)

wherein $R_1$ represents independently alkyl having 1 to 10 carbon atoms or alkoxy having 1 to 10 carbon atoms.

8 Claims, No Drawings

CHOLESTERIC LIQUID CRYSTAL COMPOSITION

CROSS REFERENCE TO RELATED APPLICATIONS

This application claims priority under 35 U.S.C. §119 to Japanese Patent Application No. JP 2007-009270, filed Jan. 18, 2007, which application is expressly incorporated herein by reference in its entirety.

BACKGROUND OF THE INVENTION

1. Field of the Invention

The invention relates to a cholesteric liquid crystal composition which reflects light of a specific wavelength in the vicinity of room temperature and body temperature and uses thereof.

2. Description of the Related Art

A cholesteric liquid crystal molecule has a spiral structure in a liquid crystal state. Accordingly, when a cholesteric liquid crystal phase is irradiated with light, it reflects a circular polarizing light of a specific wavelength corresponding to a spiral rotational direction of the liquid crystal molecule and a length of the pitch. For example, when irradiated with a visible light, it reflects selectively lights having wavelengths of blue, green, yellow and red corresponding to a length of a pitch in the liquid crystal. The color tones thereof are different from those of pigments and dyes which take on colors by absorption of lights and have a visual dependency in which a color tone changes according to viewing angles. Further, a length of a pitch in cholesteric liquid crystal can be controlled by temperature and the kind of compounds, and therefore it can selectively reflect not only visible lights but also lights of near infrared and ultraviolet regions.

There have been materials which selectively reflect lights of various wavelengths in a broad wavelength region making use of the characteristics of the cholesteric liquid crystal. They are, for example, liquid crystal pigments, coating materials, spray inks, print inks, cosmetics, printed matters for preventing counterfeit, ornamental articles and the like. Further, they are proposed as well for polarizing plates in optical devices such as liquid crystal displays and holographic devices, compensation plates, optical films such as color filters and the like. In the case of a cholesteric liquid crystal pigment which is an existing material, flake-shaped cholesteric liquid crystal polymers and microencapsulated cholesteric liquid crystal are used. The uses thereof include coating materials for cars, cosmetic ingredients and the like.

JP S61-1015 B/1986 (Patent Document 1; JP S56-92836 A/1981) describes that an optically active menthol compound is used as an additive for shortening a pitch of a liquid crystal composition without extremely reducing a clearing point of the composition. Further, the uses of such cholesteric liquid crystal material include display parts of thermometers, wrist watches and calculators.

JP S63-34918 B/1988 (Patent Document 2; JP S57-40581 A/1982) describes that an L-menthol compound is used for a component of a guest-host liquid crystal display as a pitch controlling agent.

JP H16-137158 A/2004 (Patent Document 3) describes that an optically active menthol compound as a chiral dopant for a liquid crystal composition which is used as a liquid crystal display unit is a material maintaining a lower viscosity as compared with those of other chiral agents such as cholesterol derivatives and the like.

Examples of applications of liquid crystal materials in which a color of the material is changed irreversibly by temperature to inks are described in GB2280681A (Patent Document 4; U.S. Pat. No. 5,705,093), and a thermochromic liquid crystal material including an optically active menthol derivative and a nematic liquid crystal material is disclosed therein as the above liquid crystal material. Further, the possibility of application thereof to cosmetics such as lip rouges, eye shadows and the like making use of such thermochromic characteristics is indicated as well in Patent Document 4.

When a cholesteric material is used for application particularly in cosmetic ingredients coated on lips and skins in the cosmetic field, a material showing a cholesteric reflection color in the vicinity of room temperature and body temperature is required. Red to purple, preferably red to yellow colors are required to be developed in a temperature range in the vicinity of 0 to 60° C., particularly preferably 20 to 40° C. As described above, a range of developed color versus temperature is required to be controlled in order to allow a cholesteric liquid crystal material to exhibit an effect of aesthetic decoration in cosmetic use.

A mixing example of Mixture B of three components which has a clearing point of 91.1° C. and a menthol derivative is shown in Example 3 of Patent Document 4, and a composition example of nine components including two kinds of menthol derivatives is shown in Example 5. However, a range of developed color versus a cholesteric liquid crystal phase area and temperature is not described, and informations which can be applied to materials for cosmetic ingredients are not disclosed.

SUMMARY OF THE INVENTION

The invention relates to a cholesteric liquid crystal composition including at least one compound selected from the group of compounds represented by Formulas (1) to (8) as a first component, at least one compound selected from the group of compounds represented by Formulas (9) and (10) as a second component and at least one compound selected from the group of compounds represented by Formulas (11) to (18) as a third component:

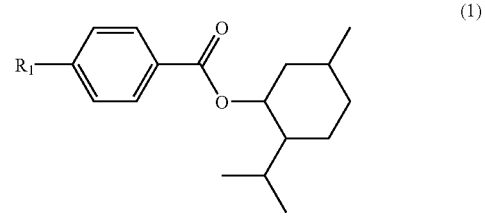

(1)

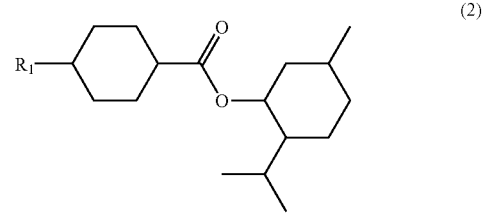

(2)

-continued

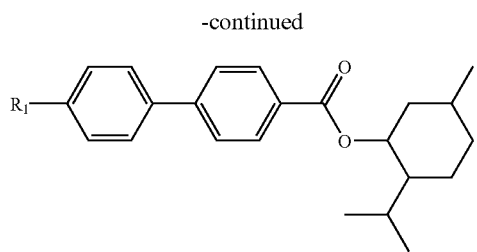
(3)

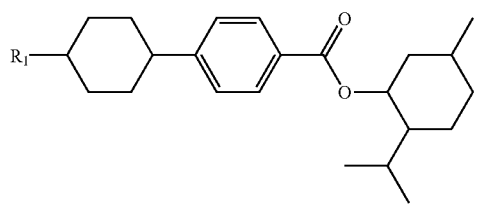
(4)

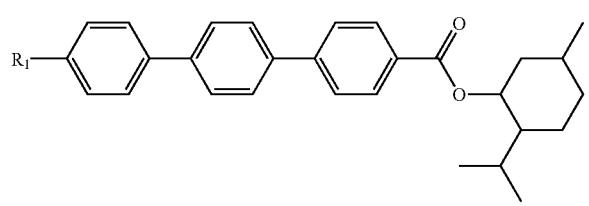
(5)

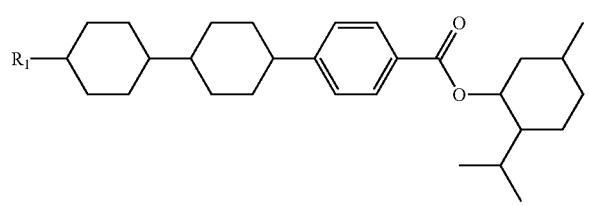
(6)

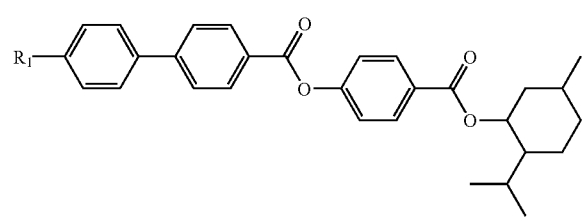
(7)

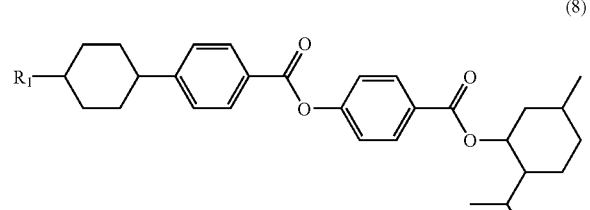
(8)

wherein $R_1$ represents independently alkyl having 1 to 10 carbon atoms or alkoxy having 1 to 10 carbon atoms;

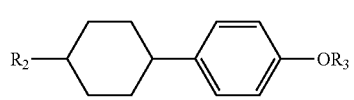
(9)

-continued

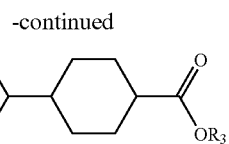
(10)

wherein $R_2$ and $R_3$ each represent independently alkyl having 1 to 10 carbon atoms;

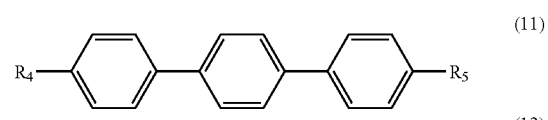
(11)

(12)

(13)

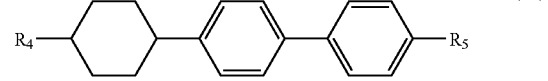

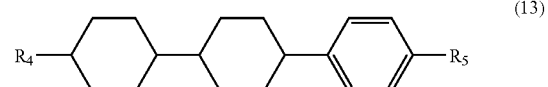

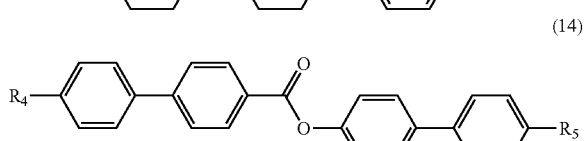
(14)

(15)

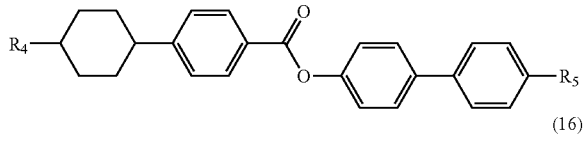
(16)

(17)

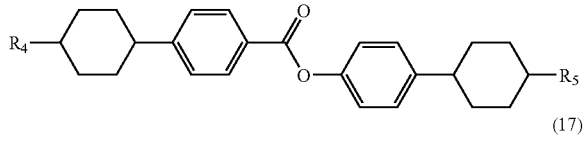
(18)

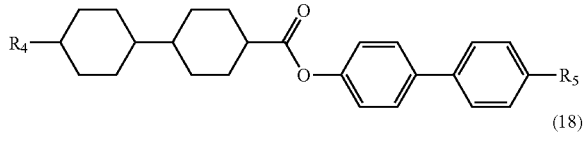

wherein $R_4$ and $R_5$ each represent independently alkyl having 1 to 10 carbon atoms or alkoxy having 1 to 10 carbon atoms.

DETAILED DESCRIPTION OF THE INVENTION

It has been found that a cholesteric liquid crystal composition including a specific optically active menthol compound and showing a selected reflection color of red to purple, more preferably red to yellow colors in a temperature range in the vicinity of particularly room temperature and body temperature exhibits a high aesthetic decoration effect when coated on lips and skins in the form of a cosmetic. The invention includes:

[1] A cholesteric liquid crystal composition including at least one compound selected from the group of compounds represented by Formulas (1) to (8) as a first component, at least one compound selected from the group of compounds represented by Formulas (9) and (10) as a second component and at least one compound selected from the group of compounds represented by Formulas (11) to (18) as a third component:

(1)
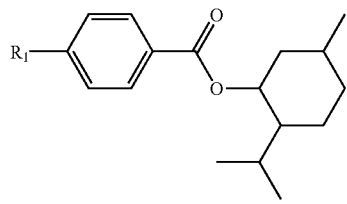

(2)
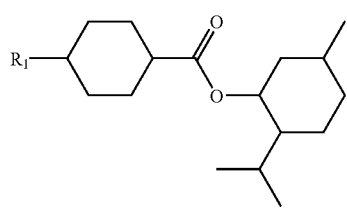

(3)
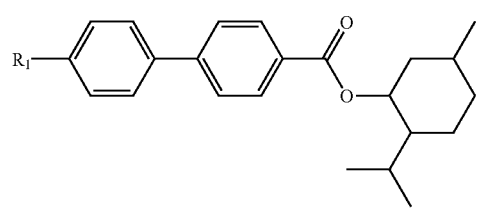

(4)
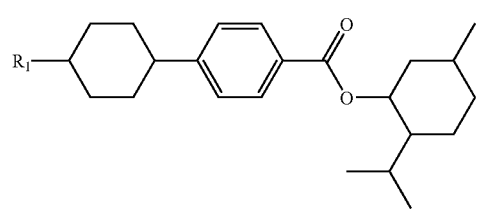

(5)
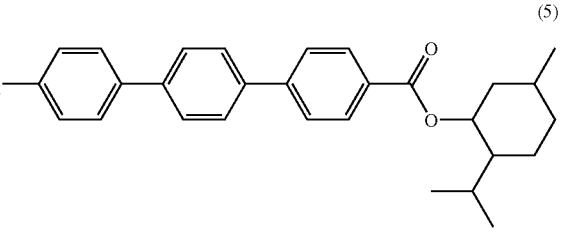

(6)
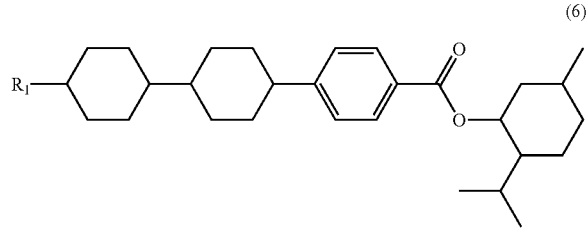

(7)
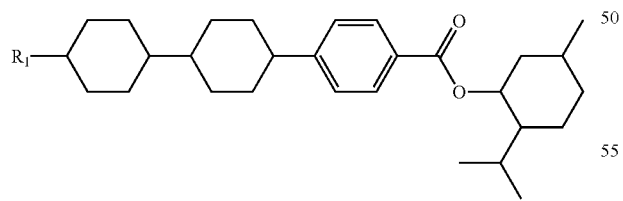

(8)
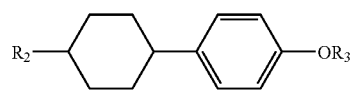

wherein $R_1$ represents independently alkyl having 1 to 10 carbon atoms or alkoxy having 1 to 10 carbon atoms;

(9)
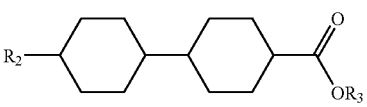

(10)

wherein $R_2$ and $R_3$ each represent independently alkyl having 1 to 10 carbon atoms;

(11)

(12)
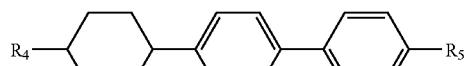

(13)
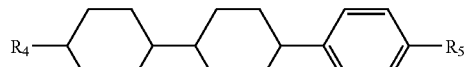

(14)
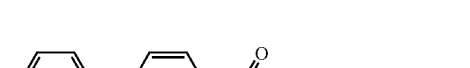

(15)
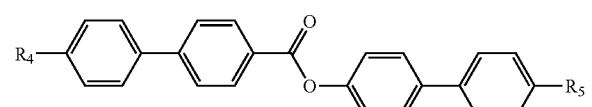

(16)
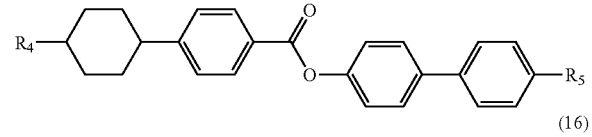

(17)
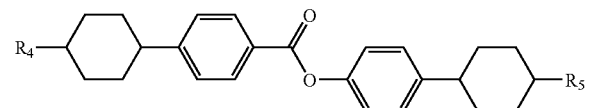

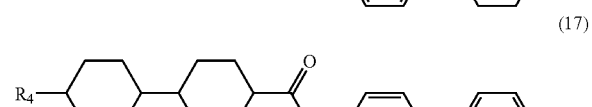

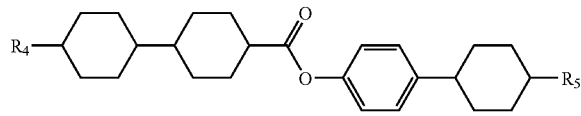
(18)

wherein $R_4$ and $R_5$ each represent independently alkyl having 1 to 10 carbon atoms or alkoxy having 1 to 10 carbon atoms.

[2] The cholesteric liquid crystal composition as described in item [1], wherein assuming that the total amount of the first component, the second component and the third component is 100 parts by weight, the first component is contained in an amount of approximately 5 to approximately 30 parts by weight; the second component is contained in an amount of approximately 15 to approximately 80 parts by weight; and the third component is contained in an amount of approximately 10 to approximately 70 parts by weight.

[3] The cholesteric liquid crystal composition as described in item [1], wherein assuming that the total amount of the first component, the second component and the third component is 100 parts by weight, the first component is contained in an amount of approximately 15 to approximately 25 parts by weight; the second component is contained in an amount of approximately 20 to approximately 60 parts by weight; and the third component is contained in an amount of approximately 10 to approximately 60 parts by weight.

[4] The cholesteric liquid crystal composition as described in item [1], including at least one compound selected from the group of the compounds represented by Formulas (4) to (6) as the first component, at least one compound selected from the group of the compounds represented by Formulas (9) and (10) as the second component and at least one compound selected from the group of the compounds represented by Formulas (13) and (18) as the third component.

[5] The cholesteric liquid crystal composition as described in item [1], further including at least one compound selected from the group of fatty acid esters, hydrocarbons, higher alcohols, lower alcohols, polyhydric alcohols, silicone oils, cyclic ethers, ketones, amides, amino acids and organic amines.

[6] Use of the cholesteric liquid crystal composition as described in items [1] to [5] for application in at least one of liquid crystal pigments, coating materials, spray inks, print inks, cosmetics, printed matters for preventing counterfeit and ornamental articles.

[7] A cosmetic including the cholesteric liquid crystal composition as described in items [1] to [5].

[8] The cosmetic as described in item [5], further including at least one solvent selected from the group of solvent selected from fatty acid esters, hydrocarbons, polyhydric alcohols, water, water-soluble high polymers and polysaccharides.

According to the invention, a liquid crystal composition is obtained that shows a cholesteric phase in the vicinity of room temperature and body temperature and can control a reflection color in a cholesteric reflection zone over a wide range of red, green, blue and purple colors by changing the composition and which shows an aesthetic decoration effect when coated on lips and skins and a cosmetic including the composition.

The cholesteric liquid crystal composition according to the invention and uses thereof shall be explained below in details. As used herein, the compound represented by Formula (1) shall be referred to as the "compound (1)," and the compounds represented by the other formulas shall be referred to in the same abbreviation.

Cholesteric Liquid Crystal Composition

The cholesteric liquid crystal composition includes at least one compound selected from the group of the compound (1) to the compound (8) as the first component, at least one compound selected from the group of the compound (9) and the compound (10) as the second component and at least one compound selected from the group of the compound (11) to the compound (18) as the third component.

The cholesteric liquid crystal composition has a wide cholesteric liquid crystal phase in the vicinity of room temperature (about 10 to 40° C.), and a wavelength area of light reflected by the cholesteric phase can be controlled by changing a composition ratio of the respective constitutional components.

$R_1$ in Formulas (1) to (8) and $R_4$ and $R_5$ in Formulas (11) to (18) each are independently alkyl having 1 to 10 carbon atoms or alkoxy having 1 to 10 carbon atoms, preferably alkyl having 1 to 5 carbon atoms or alkoxy having 1 to 5 carbon atoms. $R_2$ and $R_3$ in Formulas (2) to (3) each are independently alkyl having 1 to 10 carbon atoms, preferably alkyl having 1 to 5 carbon atoms.

The compounds (1) to (8) used as the first component for the cholesteric liquid crystal composition are optically active menthol derivatives, and they have a good compatibility with other components and can exhibit a helical pitch according to the purposes. The liquid crystal composition preferably includes at least one compound selected from the compounds (4) to (6) as the first component from the viewpoint of enhancing an upper limit temperature in a color change temperature area of the liquid crystal composition in the vicinity of room temperature.

The compounds (9) and (10) used as the second component of the cholesteric liquid crystal composition can reduce a lower limit temperature in a color change temperature area of the liquid crystal composition. The liquid crystal composition preferably includes at least one compound (9) as the second component from the viewpoint of broadening a color change temperature area of the liquid crystal composition.

The compounds (11) to (18) used as the third component of the cholesteric liquid crystal composition can enhance an upper limit temperature in a color change temperature area of the liquid crystal composition. The liquid crystal composition preferably includes at least one compound selected from the compounds (11), (13), (16) and (18), more preferably at least one compound selected from the compounds (13) and (18) as the third component from the viewpoint of preventing the liquid crystal composition from separating and showing a good compatibility.

Assuming that the total amount of the first component, the second component and the third component is 100 parts by weight, the cholesteric liquid crystal composition of the invention includes the first component in an amount of preferably approximately 5 to approximately 30 parts by weight, more preferably approximately 10 to approximately 30 parts by weight and further preferably approximately 15 to approximately 25 parts by weight, the second component in an amount of preferably approximately 15 to approximately 80 parts by weight, more preferably approximately 20 to approximately 60 parts by weight and further preferably approximately 30 to approximately 60 parts by weight and the third component in an amount of preferably approximately 10 to approximately 70 parts by weight, more preferably approximately 10 to approximately 60 parts by weight and further preferably approximately 15 to approximately 55 parts by weight.

The synthetic scheme of the compound (4) out of the compounds (1) to (8) shall be shown in the following Scheme 1. The compounds (1) to (8) can be synthesized in the same manner as in the Scheme 1 shown below.

Scheme 1: Synthesis of Compound (4)

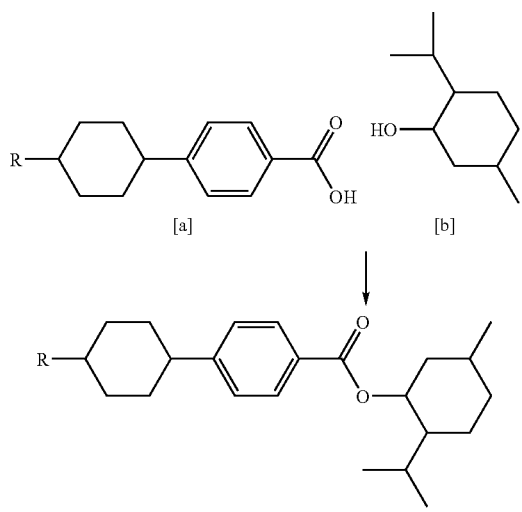

As shown in the Scheme 1, the compound (4) can be synthesized by esterification of dicyclic carboxylic acid [a] with L-menthol [b] of the same amount as that of the dicyclic carboxylic acid. In synthesis of the compound (6), tricyclic carboxylic acid [c] shown below is used in place of the dicyclic carboxylic acid to carry out the same esterification reaction.

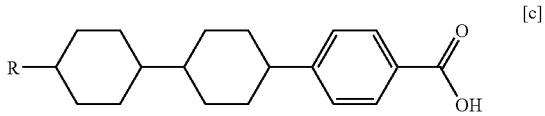

The compounds (9) to (18) can be synthesized by suitably combining synthetic methods in organic chemistry which are described in Houben Wyle (METHODEN DER ORGANISCHEN CHEMIE, Georg Thieme Verlag, Stuttgart), ORGANIC REACTIONS (John Wily & Sons Inc.), ORGANIC SYNTHESES (John Wily & Sons, Inc.), COMPREHENSIVE ORGANIC SYNTHESIS (Pergamon Press) and NEW EXPERIMENTAL CHEMISTRY COURSE (Maruzen).

The preferred embodiment of the cholesteric liquid crystal composition of the invention includes, for example:

1. the composition including the compound (3) as the first component, the compound (9) as the second component and the compound (13) as the third component;

2. the composition including the compound (3) as the first component, the compounds (9) and (10) as the second component and the compound (13) as the third component;

3. the composition including the compound (3) as the first component, the compounds (9) and (10) as the second component and the compounds (13) and (18) as the third component;

4. he composition including the compound (4) as the first component, the compound (9) as the second component and the compound (13) as the third component;

5. the composition including the compound (4) as the first component, the compounds (9) and (10) as the second component and the compound (13) as the third component;

6. the composition including the compound (4) as the first component, the compounds (9) and (10) as the second component and the compounds (13) and (18) as the third component;

7. the composition including the compound (6) as the first component, the compound (9) as the second component and the compound (13) as the third component;

8. the composition including the compound (6) as the first component, the compounds (9) and (10) as the second component and the compound (13) as the third component; and 9. the composition including the compound (6) as the first component, the compounds (9) and (10) as the second component and the compounds (13) and (18) as the third component.

The liquid crystal composition of the invention may include a solvent. The solvent includes, for example, fatty acid esters, hydrocarbons, higher alcohols, lower alcohols, polyhydric alcohols, silicone oils, cyclic ethers, ketones, amides, amino acids and organic amines. The solvent may be used alone or in a mixture of two or more kinds thereof.

Uses

The uses of the cholesteric liquid crystal composition of the invention include general coloring materials, for example, liquid crystal pigments, coating materials, spray inks, print inks and the like. Further, it can be used as well for cosmetic ingredients, printed matters for preventing forgery and decorative matters. It can be used for the cosmetic ingredients out of the above uses since it shows a selected reflection color of red to purple, preferably red to yellow colors in a temperature range in the vicinity of room temperature and body temperature.

The cosmetic ingredient of the invention contains the liquid crystal composition of the invention described above. Further, it may contain, in addition to the liquid crystal composition, components used for general cosmetics, for example, extender pigments, colorants, antioxidants, antioxidant auxiliaries, UV absorbers, metal ion masking agents, surfactants, storage stabilizers, antiseptic agents, diluents, plasticizers, moisturizing agents, viscosity controllers, feeling controllers, thickeners, film agents, ester oils, liquid fats and oils, solid fats and oils, waxes, water-soluble high polymers, cyclic ethers, ketones, amides, amino acids, organic amines, polyhydric alcohols, polysaccharides, high molecular emulsions, pH controllers, vitamins, skin nutritional supplements, fragrances, water, various extracted essences and the like according to uses as long as the effects of the invention are not damaged.

The extender pigments include, for example, barium sulfate, barium carbonate, calcium carbonate, magnesium carbonate, silica, titanium oxide, mica, sericite, talc and the like. These extender pigments may be used alone or in combination of two or more kinds thereof.

The colorants include, for example, soluble azo, insoluble azo, polyazo, phthalocyanine, anthraquinone, thioindigo, perylene, perinone, dioxazine, quinacridone, isoindolinone, quinophthalone, diketopyrrolopyrrole, anthraquinone, perinone, quinophthalone, azo, carbon black and the like.

The antioxidants include, for example, 2,2-methylenebis (4-methyl-6-t-butylphenol), 2,6-di-t-butyl-4-methylphenol (BHT) and the like.

The UV absorbers include, for example, 2-(3-t-butyl-5-methyl-2-hydroxyphenyl)-5-chlorobenzotriazole, alkoxybenzophenones and the like.

The moisturizing agents include, for example, hydrocarbons, fats and oils, waxes, hardened oils, ester oils, fatty acids, lower alcohols, glycols, glycerols, higher alcohols, silicone oils, fluorine base oils, lanolin derivatives, vegetable sterol derivatives and the like regardless of origins in animal oils, vegetable oils, synthetic oils and the like and properties of solid oils, semisolid oils, liquid oils, flammable oils and the like.

They include, to be specific, hydrocarbons such as liquid paraffins, squalane, vaseline, polyisobutylene, polybutene, paraffin waxes, ceresin waxes, microcrystalline waxes, montan waxes, Fisher-Tropsch waxes and the like; fats and oils such as Japan tallow, olive oils, castor oils, mink oils, macadamia nut oils and the like; waxes such as yellow beeswax, carnauba wax, candelilla wax, whale wax and the like; ester oils such as jojoba oil, cetyl isooctanoate, isopropyl myristate, isopropyl palmitate, octyldodecyl myristate, glyceryl trioctanoate, diglyceryl diisostearate, diglyceryl triisostearate, glyceryl tribehenoate, rosin acid pentaerythritol ester, neopentyl glycol dioctanoate, cholesterol fatty acid ester, N-lauroyl-L-glutamic acid di(cholesteryl.behenyl.octyldodecyl) and the like; fatty acids such as stearic acid, lauric acid, myristic acid, behenic acid, isostearic acid, oleic acid, 12-hydroxystearic acid and the like; higher alcohols such as stearyl alcohol, cetyl alcohol, lauryl alcohol, oleyl alcohol, isostearyl alcohol, behenyl alcohol and the like; silicone oils such as lower polymerization degree dimethylpolysiloxane, higher polymerization degree dimethylpolysiloxane, methylphenylpolysiloxane, decamethylcyclopentasiloxane, octamethylcyclotetra siloxane, fluorine-modified silicone and the like; fluorine base oils such as perfluoropolyether, perfluorodecane, perfluorooctane and the like; lanolin derivatives such as lanolin, lanolin acetate, lanolin fatty acid isopropyl, lanolin alcohol and the like; sitosterol derivatives; campesterol derivatives; stigmasterol derivatives; alcohols such as ethanol, isopropyl alcohol and the like; glycols such as propylene glycol, 1,3-butylene glycol, dipropylene glycol, polyethylene glycol and the like; glycerols such as glycerin, diglycerin, polyglycerin and the like; sorbit and the like. They may be used alone or in combination of two or more kinds thereof.

The viscosity controllers and the feeling controllers include, for example, vegetable base high polymers (for example, gum arabic, tarragacant gum, galactan, guar gum, carob gum, karaya gum, carrageenan, pectin, agar, quince seed (marmelo), algae colloid (marine algae extract), starch (rice, corn, potato and wheat), glycyrrhizinic acid, hyaluronic acid, hyaluronic acid derivatives), microbial high polymers (for example, xanthane gum, dextran, succinoglucan, pullulan and the like), animal base high polymers (for example, collagen, casein, albumin, gelatin and the like).

The semi-synthetic water-soluble high polymers include, for example, starch base high polymers (for example, carboxymethyl starch, methylhydroxypropyl starch and the like); cellulose base high polymers (for example, methyl cellulose, ethyl cellulose, methylhydroxypropyl cellulose, hydroxyethyl cellulose, cellulose sodium sulfate, hydroxypropyl cellulose, carboxymethyl cellulose, carboxymethyl cellulose sodium, crystalline cellulose, cellulose powder and the like); alginic acid base high polymers (for example, sodium alginate, alginic acid propylene glycol ester and the like); sodium hyaluronate and the like.

The synthetic water-soluble high polymers include, for example, vinyl base high polymers (for example, polyvinyl alcohol, polyvinyl methyl ether, polyvinylpyrrolidone, carboxyvinyl polymers and the like); polyoxyethylene base high polymers (for example, polyoxyethylene-polyoxypropylene copolymers of polyethylene glycol and the like); acryl base high polymers (for example, poly-sodium acrylate, polyethyl acrylate, polyacrylamide and the like); polyethyleneimine; cationic polymers and the like.

The thickeners include, for example, gum arabic, carrageenan, karaya gum, tarragacant gum, carob gum, quince seed (marmelo), casein, dextrin, gelatin, sodium pectinate, sodium alginate, methyl cellulose, ethyl cellulose, CMC, hydroxyethyl cellulose, hydroxypropyl cellulose, PVA, PVM, PVP, poly-sodium acrylate, carboxyvinyl polymers, locust bean gum, guar gum, tamarind gum, dialkyldimethylammonium sulfate cellulose, xanthane gum, magnesium aluminum silicate, bentonite, hectorite, Al Mg silicate (veegum), laponite, silicic anhydride, chondroitin sodium sulfate, carboxyvinyl polymers, alkyl-modified carboxyvinyl polymers and the like.

The cosmetic ingredient of the invention can suitably be used, for example, for rouges, lip creams, lip gloss, eye shadows, eye liners, mascara, cheek rouges, liquid foundations and the like.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

The invention shall more specifically be explained below with reference to examples, but the invention shall by no means be restricted by these examples.

Example 1

A composition including 19% by weight of a compound (component 1-1) in which $R_1$ is $C_5H_{11}$ in Formula (4), 14% by weight of a compound (component 2-1) in which $R_2$ is $C_3H_7$ and $R_3$ is $C_2H_5$ in Formula (9), 3% by weight of a compound (component 2-2) in which $R_2$ is $C_5H_{11}$ and $R_3$ is $C_2H_5$ in Formula (9), 21% by weight of a compound (component 2-3) in which $R_2$ is $C_3H_7$ and $R_3$ is methyl in Formula (10), 7% by weight of a compound (component 3-1) in which $R_4$ is $C_3H_7$ and $R_5$ is methoxy in Formula (13), 14% by weight of a compound (component 3-2) in which $R_4$ is $C_3H_7$ and $R_5$ is $OC_3H_7$ in Formula (13), 11% by weight of a compound (component 3-3) in which $R_4$ is $C_3H_7$ and $R_5$ is $C_3H_7$ in Formula (18) and 11% by weight of a compound (component 3-4) in which $R_4$ is $C_3H_7$ and $R_5$ is $C_5H_{11}$ in Formula (18) showed a red cholesteric reflection color in a temperature range of 20 to 40° C.

Examples 2 to 5

Compositions shown in Table 1 were prepared to observe reflection colors in the same manner as in Example 1.

Comparative Examples 1 to 3

Compositions shown in Table 1 were prepared to observe reflection colors in the same manner as in Example 1.

TABLE 1

|  |  | Example | | | | | Comparative Example | | |
|---|---|---|---|---|---|---|---|---|---|
|  |  | 1 | 2 | 3 | 4 | 5 | 1 | 2 | 3 |
| Component | 1-1 | 19 | 22 | 25 | 22 | 28 | 20 | 20 | 20 |
| (% by weight) | 2-1 | 14 | 16 | 15 | 9 | 8 | 80 | 40 | 40 |
|  | 2-2 | 3 |  |  | 9 | 8 |  | 40 |  |
|  | 2-3 | 21 | 16 | 15 | 14 | 13 |  |  | 40 |
|  | 3-1 | 7 | 7 | 8 | 14 | 13 |  |  |  |
|  | 3-2 | 14 | 15 | 15 | 18 | 17 |  |  |  |
|  | 3-3 | 11 | 12 | 11 | 14 | 13 |  |  |  |
|  | 3-4 | 11 | 12 | 11 |  |  |  |  |  |
| Reflection Color | 22° C. | orange | orange | green | red | orange | crystal | <0 | <0 |
|  | 35° C. | red | red | red |  |  | crystal | <0 | <0 |

Note:
<0: reflection color was shown at room temperature or lower

As shown in Table 1, the cholesteric liquid crystal compositions of the invention (Examples 1 to 5) including the component 1, the component 2 and the component 3 showed a cholesteric reflection color in the vicinity of room temperature. On the other hand, the compositions prepared in Comparative Examples 1 to 3 which did not contain the component 3 were crystallized at room temperature or showed a cholesteric reflection color at room temperature or lower.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

What is claimed is:

1. A cholesteric liquid crystal composition comprising at least one compound selected from the group of compounds represented by Formulas (1) to (8) as a first component, at least one compound selected from the group of compounds represented by Formulas (9) and (10) as a second component and at least one compound selected from the group of compounds represented by Formulas (11) to (18) as a third component:

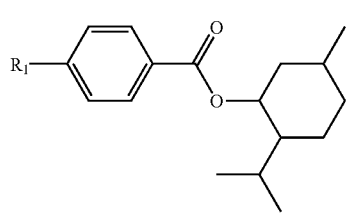

(1)

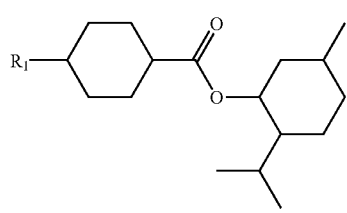

(2)

-continued

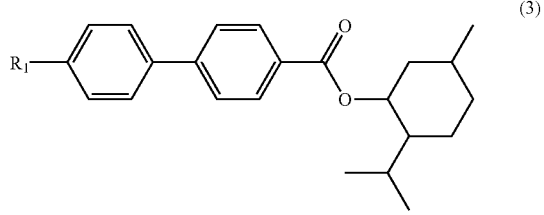

(3)

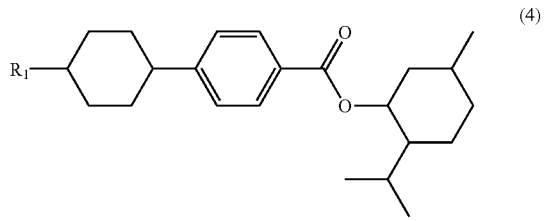

(4)

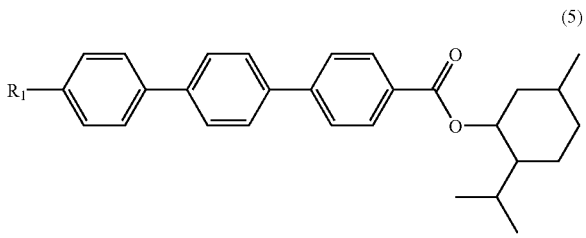

(5)

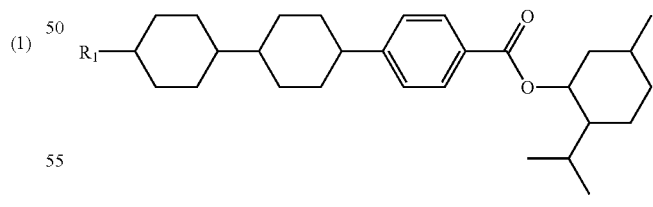

(6)

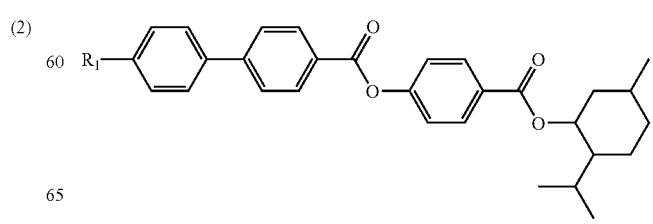

(7)

-continued

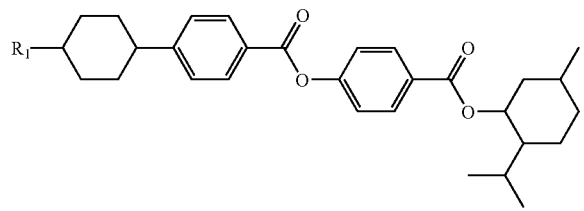

(8)

wherein $R_1$ represents independently alkyl having 1 to 10 carbon atoms or alkoxy having 1 to 10 carbon atoms;

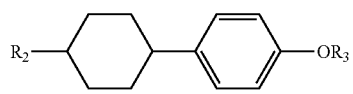

(9)

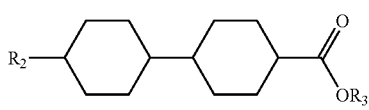

(10)

wherein $R_2$ and $R_3$ each represent independently alkyl having 1 to 10 carbon atoms;

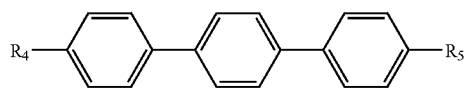

(11)

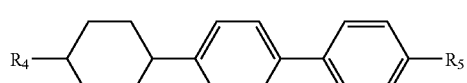

(12)

(13)

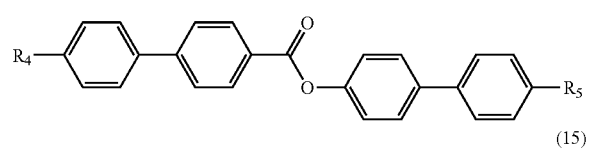

(14)

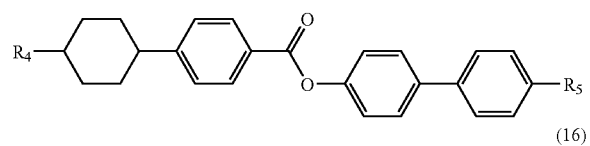

(15)

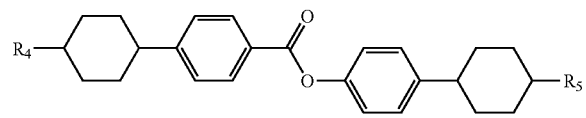

(16)

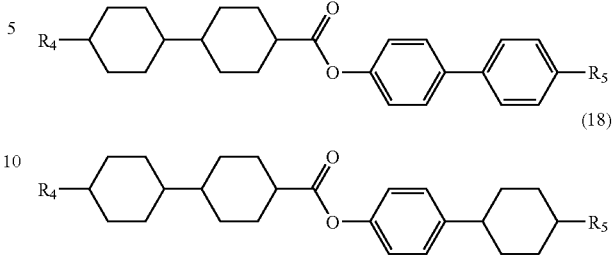

(17)

(18)

wherein $R_4$ and $R_5$ each represent independently alkyl having 1 to 10 carbon atoms or alkoxy having 1 to 10 carbon atoms.

2. The cholesteric liquid crystal composition of claim 1, wherein when the total amount of the first component, the second component and the third component is 100 parts by weight, the first component is contained in an amount of approximately 5 to approximately 30 parts by weight; the second component is contained in an amount of approximately 15 to approximately 80 parts by weight; and the third component is contained in an amount of approximately 10 to approximately 70 parts by weight.

3. The cholesteric liquid crystal composition of claim 1, wherein when the total amount of the first component, the second component and the third component is 100 parts by weight, the first component is contained in an amount of approximately 10 to approximately 30 parts by weight; the second component is contained in an amount of approximately 20 to approximately 60 parts by weight; and the third component is contained in an amount of approximately 10 to approximately 60 parts by weight.

4. The cholesteric liquid crystal composition of claim 1, comprising at least one compound selected from the group of the compounds represented by Formulas (4) to (6) as the first component, at least one compound selected from the group of the compounds represented by Formulas (9) and (10) as the second component and at least one compound selected from the group of the compounds represented by Formulas (13) and (18) as the third component.

5. The cholesteric liquid crystal composition of claim 1, further comprising at least one compound selected from the group of fatty acid esters, hydrocarbons, higher alcohols, lower alcohols, polyhydric alcohols, silicone oils, cyclic ethers, ketones, amides, amino acids, organic amines and combinations thereof.

6. A method for using the cholesteric liquid crystal composition of claim 1 comprising: constructing at least one object selected from the group consisting of a liquid crystal pigment, coating materials, spray inks, print inks, cosmetics, printed matters for preventing counterfeit and ornamental articles.

7. A cosmetic ingredient comprising the cholesteric liquid crystal composition of claim 1.

8. The cosmetic ingredient of claim 7, further comprising at least one solvent selected from the group of fatty acid esters, hydrocarbons, polyhydric alcohols, water, water-soluble high polymers, polysaccharides and combinations thereof.

* * * * *